(12) United States Patent
Shmueli et al.

(10) Patent No.: US 7,761,261 B2
(45) Date of Patent: Jul. 20, 2010

(54) PORTABLE WIRELESS GATEWAY FOR REMOTE MEDICAL EXAMINATION

(75) Inventors: Ram Shmueli, Ramat Hasharon (IL); Moshe Cohen, Netanya (IL); Shai Misan, Trieste (IT)

(73) Assignee: MEDIC4ALL A.G. (IL)

( * ) Notice: Subject to any disclaimer, the term of this patent is extended or adjusted under 35 U.S.C. 154(b) by 0 days.

(21) Appl. No.: 10/552,112

(22) PCT Filed: Apr. 7, 2004

(86) PCT No.: PCT/IL2004/000316
§ 371 (c)(1),
(2), (4) Date: Oct. 30, 2006

(87) PCT Pub. No.: WO2004/090661
PCT Pub. Date: Oct. 21, 2004

(65) Prior Publication Data
US 2007/0088521 A1    Apr. 19, 2007

Related U.S. Application Data

(60) Provisional application No. 60/461,319, filed on Apr. 8, 2003.

(51) Int. Cl.
*G08B 1/08* (2006.01)
(52) U.S. Cl. .................. 702/188; 702/182; 600/301; 340/539.12

(58) Field of Classification Search .................. 702/127, 702/131, 139, 183, 187, 188; 340/359.16–539.19, 340/539.22, 539.24, 539.26; 600/301
See application file for complete search history.

(56) References Cited

U.S. PATENT DOCUMENTS

| 2,135,476 | A  | * | 11/1938 | Rugh ................... 340/539.11 |
| 5,973,603 | A  | * | 10/1999 | Judy ........................ 340/628 |
| 6,985,078 | B2 | * | 1/2006  | Suzuki et al. .......... 340/539.12 |
| 7,001,334 | B2 | * | 2/2006  | Reed et al. ................. 600/300 |
| 2002/0078367 | A1 | * | 6/2002  | Lang et al. ................. 713/200 |
| 2002/0118112 | A1 | * | 8/2002  | Lang ....................... 340/573.1 |
| 2005/0275396 | A1 | * | 12/2005 | Kitani et al. ............. 324/76.61 |
| 2006/0264775 | A1 | * | 11/2006 | Mills et al. ................. 600/547 |

* cited by examiner

*Primary Examiner*—Manuel L Barbee
(74) *Attorney, Agent, or Firm*—Smith Frohwein Tempel Greenlee Blaha, LLC; Gregory Scott Smith

(57) ABSTRACT

A remote monitoring system that includes a portable measuring device that can be coupled to a portable wireless gateway. The portable measuring device obtains measurements including physiological data, movement data and ambient measurements and provides these measurements to the portable wireless gateway. The portable wireless gateway can interface with a networked personal computer through an USB connector. Once interfaced to the computer, the measurement data can be loaded into the computer and delivered to a central system through the networked personal computer. The system enables the monitoring of a user's medical information to allow diagnostics of the user.

18 Claims, 4 Drawing Sheets

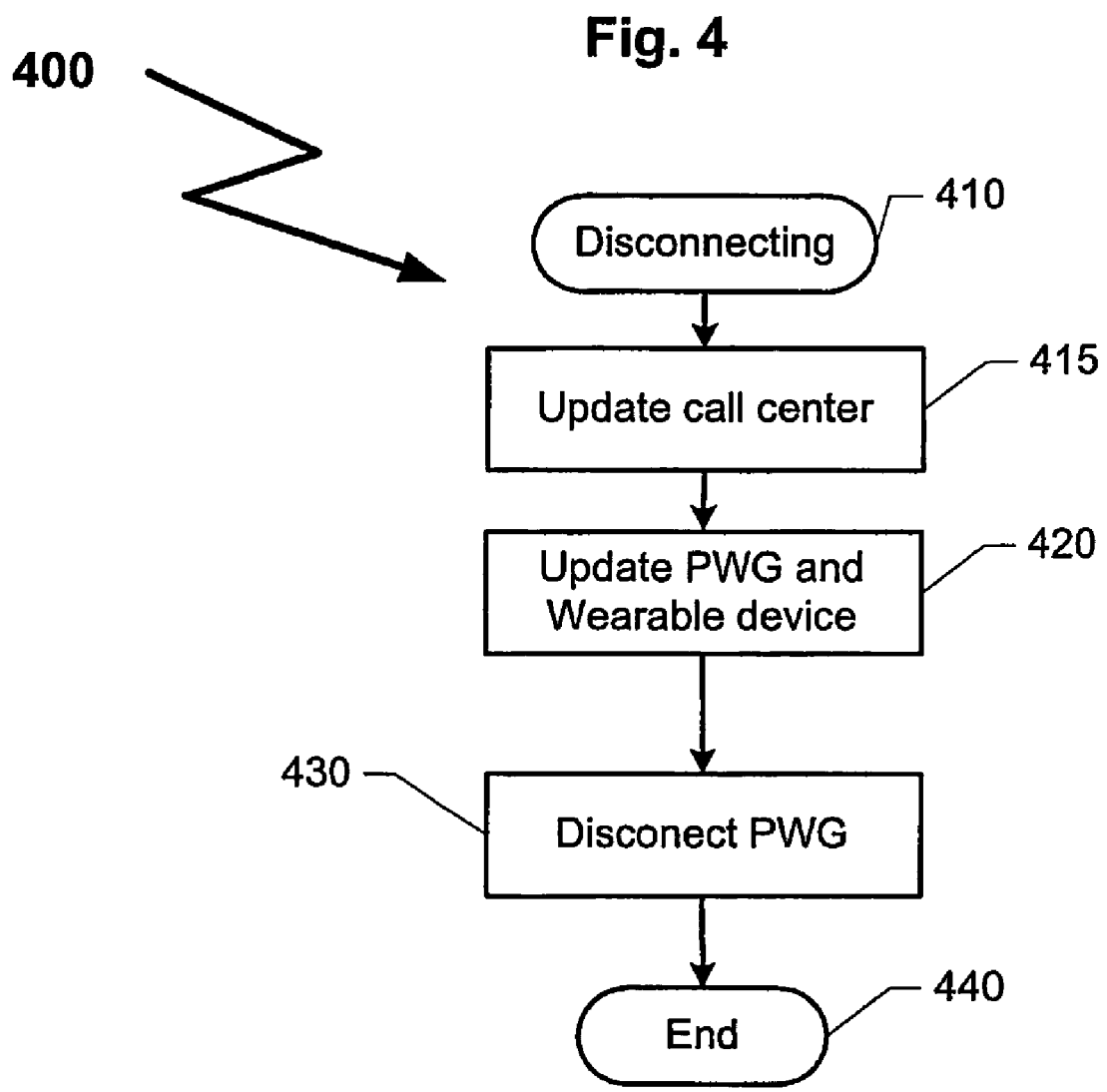

PORTABLE WIRELESS GATEWAY FOR REMOTE MEDICAL EXAMINATION

CROSS-REFERENCE TO RELATED APPLICATION

This application claims benefit under 35 U.S.C. §120 of priority from U.S. Provisional Patent Application No. 60/461,319 filed on 8 Apr. 2003, entitled, "A PORTABLE WIRELESS GATEWAY FOR REMOTE MEDICAL EXAMINATION," the subject matter of which is hereby incorporated by reference.

FIELD OF THE INVENTION

The present invention relates to the field of remote medical examinations for subjects, particularly in a non-medical environment, such as the home or office or even within an "Internet Cafe". Preferably, the present invention is operable by individuals who are not medically trained, such as by the subject himself or herself.

BACKGROUND OF THE INVENTION

Currently, a number of different types of devices are available for non-invasive monitoring of human subjects. For example, the heart function can be monitored in a subject through the use of electrodes, which must be attached to the skin of the subject. Although non-invasive, such equipment is nevertheless uncomfortable for the subject, who is attached to a network of cables and wired sensors. In addition, such equipment is very expensive, limiting its use to hospitals and other medical settings in which both the cost and the discomfort of the subject can be justified. Furthermore, discomfort and the overwhelming technological appearance of current monitoring systems may result in the subjects becoming anxious when examined by medical personnel, thereby significantly altering the normal readings for these subjects.

However, there are many different situations in which non-invasive monitoring of a human subject is desired. For example, such monitoring could be very useful as part of the overall health maintenance of the human subject, and could be used in order to detect any type of deterioration in the physiological condition of the subject before a concomitant deterioration in the health of the subject becomes noticeable. Examples of adverse physiological conditions which could be detected with regular non-invasive monitoring include, but are not limited to, excessive weight gain or weigh loss; arrhythmia and other heart conditions; incipient diabetes in the form of improper glucose metabolism; and the loss of lung capacity or other problems with respiration.

Heart rate and blood pressure are important factors in determining the state of a person's health and the physical condition of a person's body in response to physical or emotional stress. Periodic monitoring of these physical parameters is particularly important for individuals having cardiac disease and/or lowered cardiac functioning, or high blood pressure. However, physically healthy individuals may also wish to periodically monitor their heart rate and blood pressure in stressful situations, for example when engaging in strenuous exercise or in work.

In order to support regular monitoring of human subjects in their normal environment, such as in the home and at the office for example, the equipment must be non-invasive and easy to use. The equipment would then be able to monitor at least one physiological parameter of the user, without requiring the user to perform any complicated actions and/or to operate complex devices. Indeed, it would be highly preferred for the equipment to be incorporated as part of the regular daily living routine of the subject, since the requirement for any additional or special actions on the part of human subject is likely to result in decreased compliance. In addition, the equipment should be robust yet inexpensive.

For ease of use, monitoring equipment carried by the user may be used. Such monitoring equipment is required to be ready for receiving an impromptu call initiated by a medical center. However, keeping the monitoring equipment active and ready to receive a call results in reducing the lifetime of its battery. Therefore there is a need for a system that enables the Medical Service Center to make an impromptu call to the monitoring equipment, while the monitoring equipment is not active (i.e., in a sleeping mode) without losing the information that is transferred from the Medical Service Center to the monitoring equipment.

Furthermore, preferably the subject should be able to transmit the collected medical information and to communicate verbally with medical personnel. Also, medical personnel should be able to view the subject and the data being collected. In order to make the remote medical service available to wide variety of users the communication with medical personal may be carried over a common communication link such as regular telephone lines.

Common remote medical examination systems may include at least one piece of monitoring equipment carried by the user. The monitoring equipment communicates over a wireless communication channel with a gateway. On the other side, the gateway communicates to a computer at a central service center using common communication protocols such as Internet Protocol (IP) over common telephone line, ISDN etc. Such a remote medical examination system is disclosed in PCT applications PCT/IL02/00994 or in PCT/IL02/00995, the contents of which are incorporated herein by reference. The advantage of such a system is that the user may move freely and do the normal activities that he or she is used to do while the system may monitor the subject's physical conditions. However, these systems are stationary and require some installation procedure and needs. Therefore the user may enjoy the system only while staying in the site where the system is installed, for instance in the subject's home or office.

In addition each user may have some personal data, such as: user's medical file history, special measuring programs, escalation procedures etc. It can be beneficial for a user if this information may be portable with the user and valid in case that the user is far from the site in which the remote system is installed. For example, in case that the user is in hospital, the medical personal there may have access to the system as well as to the personal medical files.

Therefore there is a need for a portable system and a method for medical monitoring system that may communicate with a medical service center. Such a system will spread the opportunity of a user to benefit from his medical services in variety of locations such as home, work, hotels hospitals etc. In addition, there is a need for a system in which personal medical data may be carried by the user.

Throughout this description the term "computer" includes, but is not limited to, Personal Computer (PC), laptop, notebook, palm computer, cellular phone etc. Henceforth, the description of the present invention may use the term 'PC' as a representative term for any of the above group or similar type system.

SUMMARY OF THE INVENTION

The present invention overcomes the deficiencies of the current art by providing a wireless portable gateway that may be connected to a common connector of a PC such as Universal Serial Bus (USB) connector. On the other hand, the wireless portable gateway may communicate with at least one portable measuring equipment device by using RF communication. The RF communication may be based on standards protocols such as Bluetooth or IEEE 802.11 (wireless LAN) or on a similar or proprietary protocol.

Such a portable gateway may have the shape of a USB flash memory disk with an internal or external antenna. The product is easily carried and installed by the user using the USB plug and play capabilities.

Other embodiments of the present invention may use other types of connectors/protocols rather than the USB. For example, other embodiments may use FIREWIRE or RS232 etc. Henceforth, the description of the present invention may use the term 'USB' as a representative term for any of the above group. Furthermore, the present invention is not limited to the shape of a USB flash memory disk and other shapes may also be used. Those embodiments may be connected directly to the PC connector or via a cable or a docking station. The embodiments may use the power coming from the PC connector or from external source or battery.

The PC may communicate with the medical center over any network solution such, as but not limited to, an Internet Protocol based network such as the Internet, Intranet, LAN etc. over communication links such as a telephone line, cellular, ISDN, ADSL etc. The PC may be used as an interface node on the communication link or may also be used as the monitor and the controller of the medical examination system, at the user site. In parallel to medical examination activities the PC may perform its common tasks.

The portable wireless gateway (PWG) may have a nonvolatile memory, such as but not limited to flash memory, EEPROM, RAM, etc. In an embodiment of the present invention the nonvolatile memory may contain the operating software that runs over the PC that is used as a host PC for communicating and controlling the medical measuring system at the user's current location. Such an embodiment may have two stages during its installation. At the first stage the PWG emulates a nonvolatile memory device, such as but not limited to a USB flash memory disk. After plugging the PWG to the USB plug, the user may use it as a USB flash memory disk and loads the operating software with or without a driver to the PC or the operating software may download and initialize itself automatically into the host PC computer. Then during the second stage, the medical measuring system is activated, using the operating software that was loaded to the host computer.

In other embodiments, the nonvolatile memory may include, in addition to the operating software or instead of the operating software, personal data such as, but not limited to, personal information, medical history, medical properties, statistical data of previous measurements, data regarding the physical condition of the user, special sensitivities of the user to medicines etc. In some embodiments, part or all of the personal data may be encrypted.

Other embodiments may use external media to store the operating software. For example, an exemplary embodiment may use CD ROM to store the operating software at the user's location. In such an embodiment, the operating software is loaded first into the PC from the CD ROM and then the PWG is plugged to the PC's connector. Or in some cases, upon plugging the PWG, the PC senses that a new hardware device is plugged in and requests the user to install the operating software of the new device from the CD ROM. In other embodiment of the present invention the operating software of the medical measuring system may be downloaded via the Internet.

In some embodiments of the present invention the PWG may include authentication and/or encryption capabilities. In some embodiments, the user may configure the PC to avoid storing medical information over its local disc. Instead or simultaneously any medical information may be stored in the PWG.

In other embodiments of the present invention, the nonvolatile memory may include an authentication code for authenticating the user to the service center. Such authentication may be protected using an encryption protocol.

In some embodiments of the present invention the PC may have audiovisual capabilities enabling the user to communicate with the call center.

In some embodiments of the present invention, the PWG may also communicate with other standard wireless domestic sensors, such as smoke detectors and burglary alarms, thus the PWG may receive their transmission and activate the operation software on the PC to alert the user, for example, by sending him an SMS massage to his cellular phone or by alerting the call center using its computer network capabilities.

Thus it is evident that the present invention, by utilizing a portable wireless gateway (PWG) that can be connected to any PC (an item which is present in many houses, offices, hospitals etc.). The PC is preferably connected to the Internet, enables the owner of the PWG to enjoy the medical measuring services in a plurality of locations.

It should be noted that the terms "home", "remote", "user's site", "user's location" and "office" are used interchangeably herein and are used as examples only, in order to indicate the use of the present invention outside of a professional medical environment, and are not intended to be limiting in any way.

It should be noted that the terms "subject", "user" and "patient" are used interchangeably herein. And that the terms "Medical Service Center", "Call Center" and "Medical Center" are used interchangeably herein.

Hereinafter, the terms "microprocessor", "computational device" and "computer" includes, but is not limited to, a general-purpose microprocessor, a DSP, a micro-controller or a special ASIC, hardware, a combination of hardware and software and/or firmware, designed for that purpose.

The method of the present invention could be described as a process for being performed by a data processor, and as such could optionally be implemented as software, hardware or firmware, or a combination thereof. For the present invention, a software application could be written in substantially any suitable programming language, which could easily be selected by one of ordinary skill in the art. The programming language chosen should be compatible with the computational device (computer hardware and operating system) according to which the software application is executed. Examples of suitable programming languages include, but are not limited to, Visual Basic, Assembler, Visual C, standard C, C++ and Java.

Other objects, features, and advantages of the present invention will become apparent upon reading the following detailed description of the embodiments with the accompanying drawings and appended claims.

BRIEF DESCRIPTION OF THE DRAWINGS

The invention is herein described, by way of example only, with reference to the accompanying drawings, wherein:

FIG. 4 is an exemplary flow diagram illustrating the removal of the PWG.

DESCRIPTION OF EXEMPLARY EMBODIMENTS

Figure 1:
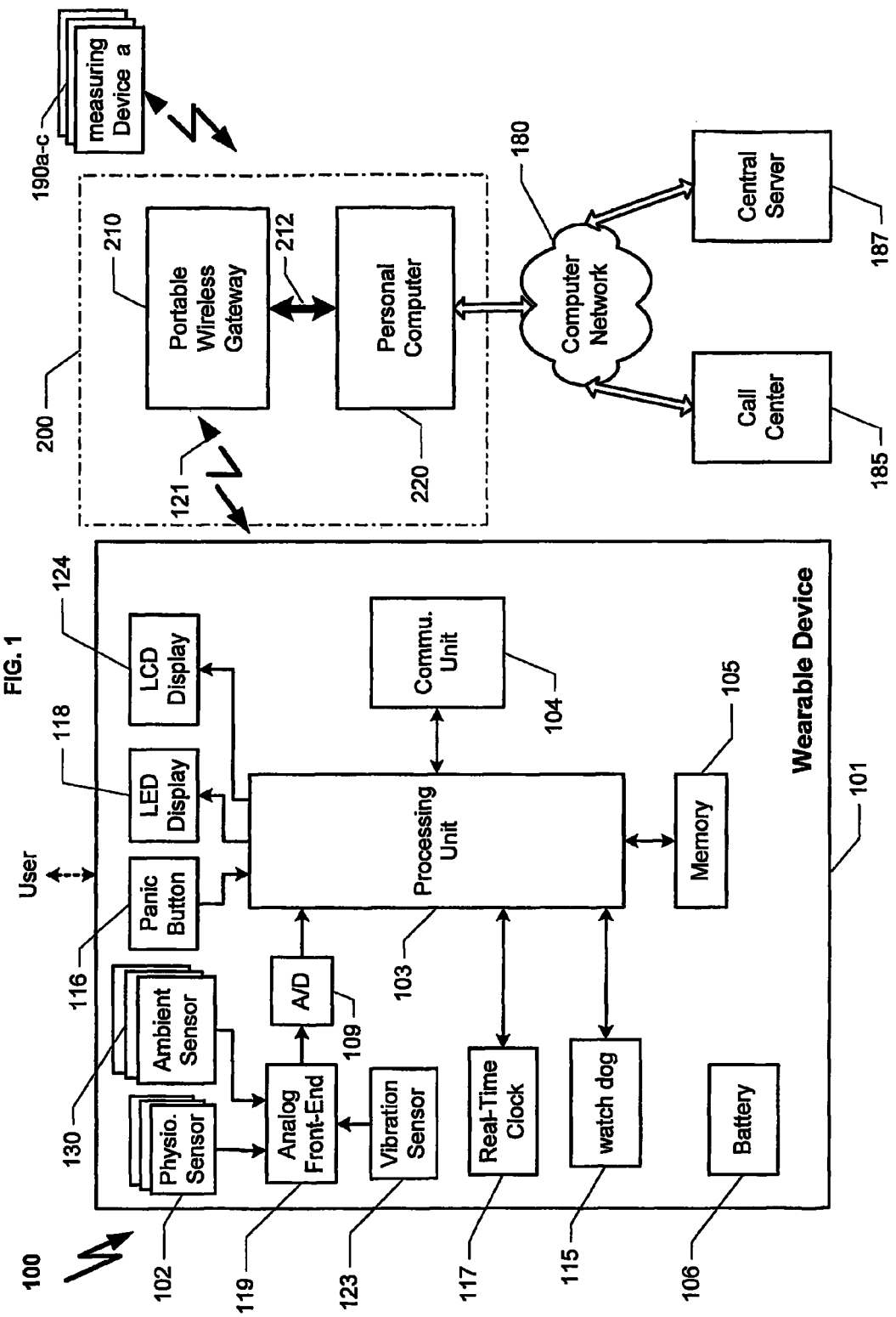
FIG. 1 is a schematic block diagram of a system according to an exemplary embodiment of the present invention.

Referring now to the drawings, in which like numerals refer to like parts throughout the several views, exemplary embodiments of the present invention are described.

The present invention is of a portable system and method for enabling medical data collection to be performed remotely, at the user location, while the user may easily carry the system, install and operate it in different locations. In each of these locations, there is a PC, which may be connected to a communication network that may access the central server, such as the Internet. In some locations in which the PC has audio/visual capabilities, the system may also permit Audio/Video conferencing between the subject and the medical personnel. Where the PC is not connected on-line to the network, it may store the medical data and forward it to the central server when the link becomes on-line, alternately it may store the data within its local disk or on the nonvolatile memory permanently or temporarily to be retrieved later by the user or by a medical personnel.

More specifically, the present invention is of an apparatus, which features bi-directional communication for transferring medical data with medical personnel operated Call Center, alternately or simultaneously, to a central server. The communication may be carried over any communication network such as the Internet via regular telephone line, ISDN, ADSL, CABLE TV, Cellular or any other type of physical network. The PC in which the apparatus is connected may be integrated with audio and video conferencing between a remote (home, "Internet Cafe" and office) subject and a medical service center. The invention is particularly useful for subjects having some type of medical risk who wishes to be supervised by a medical service center from numerous locations as long there is a PC with a USB connector or similarly functional connector and a network connection available.

According to an embodiment of the present invention, the system of the present invention features a remote apparatus and a medical service center with central server, which operates to enable remote monitoring for a subject at the home or other locations. The medical examinations may include visual and verbal communication and examinations with a two-way audio and video channel for enabling conversation between the subject and medical personnel at a medical service center.

FIG. 1 illustrates a schematic block diagram of a system according to an exemplary embodiment of the present invention. As shown, a system 100 features a wearable device 101 to be worn by a user, or a wireless medical device for measuring at least one physiological parameter of the user. Wearable device 101 may be as a wrist-mounted device, for example by being attached with a wristband or other fastening article to the wrist of the user; however, it should be understood that the device can be attached to clothing, carried in a pocket or attached to other parts of the body as well. The present invention enables such a measurement to preferably be transformed into medical information about the user. Such information may be sent through a portable wireless gateway 210 via USB connection, or similarly functional connection, 212 to PC 220. PC 220 may or may not process the received information and transfers the data over the computer network 180 to central server 187. The information may also be delivered to medical personnel (for example at a call center 185). The call center 185 and the central server 187 may be in the same site and may be connected over a LAN or INTERNET.

As previously noted, the present invention is not limited to wearable device. Other measuring equipment 190a to 190c may be used such as, but not limited to, scale, EGC, blood pressure measuring device, glucometer, smoke detectors, etc. Portable wireless gateway 210 may communicate with one or more measuring equipment devices 190a to 190c. Computer network 180 may be any network solution such as, but not limited to, Internet Protocol based network as the Internet, Intranet, LAN etc. over communication links such as telephone line, cellular, ISDN, ADSL etc. Henceforth, the description of the present invention may use the term 'Internet' as a representative term for any of the computer network solutions.

Examples of medical information which may be extracted from the measured physiological parameter or parameters include, but are not limited to: heart rate; heart rate regularity; breathing rate; arrhythmia of the heart (if any), as well as the general rhythm and functioning of the heart; blood pressure (systolic and diastolic); presence of abnormal body movements such as convulsions for example; body position; fall detection; general body movements; body temperature; presence and level of sweat; oxygen saturation in the blood; and glucose levels in the blood.

The PWG 210 may communicate with the wearable device 101 of the present invention through a wireless communication channel. The wireless communication may be based on common standards such as, but not limited to, Bluetooth, wireless LAN (IEEE 802.11) or proprietary protocol. Other embodiments may use IR communication instead of RF communication between the wearable device 101 and the PWG 210. The PWG may convert the information coming from the wearable device into the format that fit the communication over USB.

PWG 210 is described in detail herein below in conjunction with FIGS. 2, 3 and 4. Additional information about the operation of wearable device 101, call center 185 and the central server 187 is disclosed in PCT applications PCT/IL01/01187; PCT/IL02/00285; PCT/IL02/00995; PCT/IL02/00994 the contents of which are incorporated herein by reference.

In an exemplary embodiment of the present invention, the PWG, the wearable device or the medical device may also measure other parameters that may affect the subject's physical condition, including but not limited to, ambient temperature and humidity, lighting conditions, smoke and/or other material in the air, user location, distance from home etc.

The present invention may feature a manually/automatically activated medical measurement signal that may be initiated by the subject himself, by PC 220, or from the call center 185. The activate signal from the call center is transferred over the Internet 180 through PC 220 for being transmitted through the PWG 210. In same cases the activate signal may be used as alarm signal in order to indicate an emergency or otherwise dangerous situation for the user. The activate/alarm signal may optionally be transmitted in the reverse direction according to a manual action of the user, such as pressing a "panic button" 116 for example.

Most preferably, the alarm signal is transmitted automatically upon measurement of the one or more physiological parameters of the user, preferably even if the user is unable to press the panic button. Optionally, the alarm signal may be given to the user, additionally or alternatively, for example by sounding an audible alarm, more preferably from the wrist-mounted device itself. Upon receipt of manually/automatically activated medical measurement of the user, the PWG may store it on its local nonvolatile memory module 240 or transfer it the host PC 220 to be stored there on its local hard disk or to be transferred further on to the central server 187 to be stored and analyzed. PC 220, after receiving and processing the message may return the processed information to the PWG 210 in order to store in the nonvolatile memory of the PWG 210.

Upon receipt of the manually/automatically activated alarm signal via PWG 210, the PC 220 would preferably initiate immediately a call to a human operated call center 185. Then the PC 220 may instruct, via PWG 210, the user to manually activate the wearable device 101 to collect one or more current physiological measurements of the user. These measurements may be sent directly to PWG 210, or alternatively may be analyzed, in the wearable device, in order to compute the medical parameters of the user before sending the results to PC 220 via the PWG 210. The PC 220 may analyze the measurement. The human operator, at the medical center, would then preferably be able to assess the user's medical condition from the received information.

The wearable device 101 of the present invention may also monitor, at least periodically but more preferably continuously, the value or condition of one or more physiological parameters of the user. Continuous monitoring would more easily enable the device to transmit the alarm signal if measurements of one or more physiological parameters are collected and analyzed by a microprocessor to form medical information, which then could be determined to be above predefined criteria, such as unstable heart rate, or very high or low blood pressure, for example.

According to a non-limiting exemplary embodiment of the present invention, the wrist-mounted device 101 features one or more sensors attached to a wristband or other fastening article. The sensor(s) are preferably connected to a microprocessor, optionally by a wire but alternatively through a wireless connection. The microprocessor may optionally also be located within the wristband, or otherwise attached to the wristband. The sensor(s) preferably support automatic collection of at least one physiological measurement; more preferably, the microprocessor is able to execute one or more instructions for extracting clinically useful information about the user from such measurement(s).

The microprocessor more preferably operates a software program to process and analyze the data, which is collected, in order to deliver medical information. The measurement data, is then preferably transferred via PWG 210 to PC 220. The PC 220 may relay such information to a central server 187, which may be able to provide such information to medical personnel, for example as part of a call center 185. Therefore, continuous monitoring of the physiological parameters of the user may optionally and more preferably be made, enabling better medical care for the user.

A general, non-limiting example of suitable methods for measuring the heart rate and/or other heart-related physiological parameters of a subject who is wearing the device according to the present invention may be found in the article "Cuff-less Continuous Monitoring of Beat-To-Beat Blood Pressure Using Sensor Fusion", by Boo-Ho Yang, Yi Zhang and H. Harry Asada, submitted to IEEE transactions on Biomedical Engineering, 2000, hereby incorporated by reference as if fully set forth herein, where systolic and diastolic blood pressure are calculated using the pulse pressure shape per heartbeat. The disclosure does not describe a device, which has the functionality according to the present invention, but the disclosed method is generally useful for determining blood pressure from an external measurement of pressure from the pulse through the skin of the subject.

Device 101 may have at least one physiological sensor 102 for measuring at least one physiological parameter of the user, a vibration sensor 123, preferably a piezoceramic sensor, which is not in direct contact with the skin of the user. Sensor 123 measures the movement of the wrist. The output of sensor 123 can be used by a processing unit 103 to capture the movement of the wrist and to recover some noise received by sensor 102, which is caused by such movement.

Sensor 123 may be used for measuring the breath of the subject. For measuring the breath, the subject may be requested to put the hand (with the wearable device 101) over the subject's abdomen. In this position sensor 123 measures the movement of the abdomen, which is due to the subject's breath.

Device 101 may include additional ambient sensors 130 such as but not limited to a humidity sensor for measuring the ambient humidity. An exemplary humidity sensor may be the Humidity Gauge manufactured by Honeywell.

In order to support processing of the measured physiological parameter or parameters, processing unit 103 may optionally include internal RAM and non-volatile program memory (not shown). Also processing unit 103 may optionally include an extended data memory 105 located externally to processing unit 103. Processing unit 103 preferably executes at least one instruction for processing the data obtained by sensor 102.

Examples of such processing units 103 include but are not limited to PIC18LC452 by Microchip Technology Inc., which contains 10 channels of 10 bit A/D converters, a 1.5K bytes of internal RAM and 32K Bytes of non-volatile program memory.

Extended memory component 105 is preferably an electrically erasable non-volatile external memory component. Examples of such a memory component include but are not limited to FM24CL64-S (Ramtron, USA), with 64 Kbit of fast access read/write serial memory for storing temporary data related to the sampled physiological parameter.

Device 101 may have a real time clock 117 in order to provide an accurate time and date for each measurement, as device 101 can optionally store a few measurements before transmitting such data and/or information to PWG 210, as described in greater detail below. Real time clock may also optionally be used for such applications as reminding the subject to take medication, perform a prescheduled measurement, and so forth. An A/D converter 109 with multiple inputs may be utilized if sensor 102 is an analog sensor, in order to convert the analog signal to a digital signal.

Device 101 may include a display unit or units 118 and/or 124. The display unit may be used for displaying messages coming from the Call Center 185, alarm information, instructions to the user etc.

Device 101 may also optionally feature a watchdog 115, which monitors the function of device 101. If the end of a watchdog time period is reached, device 101 is assumed to have a fault in its operation, and a master reset is preferably initiated automatically.

Device 101 preferably features an internal communication unit 104, for at least unidirectional, but more preferably bi-directional, communication with PWG 210. Communication unit 104 may act as an interface module between processing unit 103 and the communication protocol that is used over the wireless connection 121 with PWG 210. In addition communication unit 104 may include the transmitter and the receiver that are used for the wireless communication 121. Communication 121 may be RF communication based on standard protocols such as Bluetooth or IEEE 802.11 (wireless LAN) or on a proprietary protocol or other wireless communication methods such as IR. In case of using an RF proprietary protocol, the communication may be in any allocated frequency band but most preferably is in the unlicensed frequency spectrum.

In order to save power and increase the life of the battery, wearable device 101 may be placed into a sleep mode for the majority of the time. The wearable device 101 can be awaked according to a prescheduled program that is sent from the medical center or by manual activation.

Figure 2:
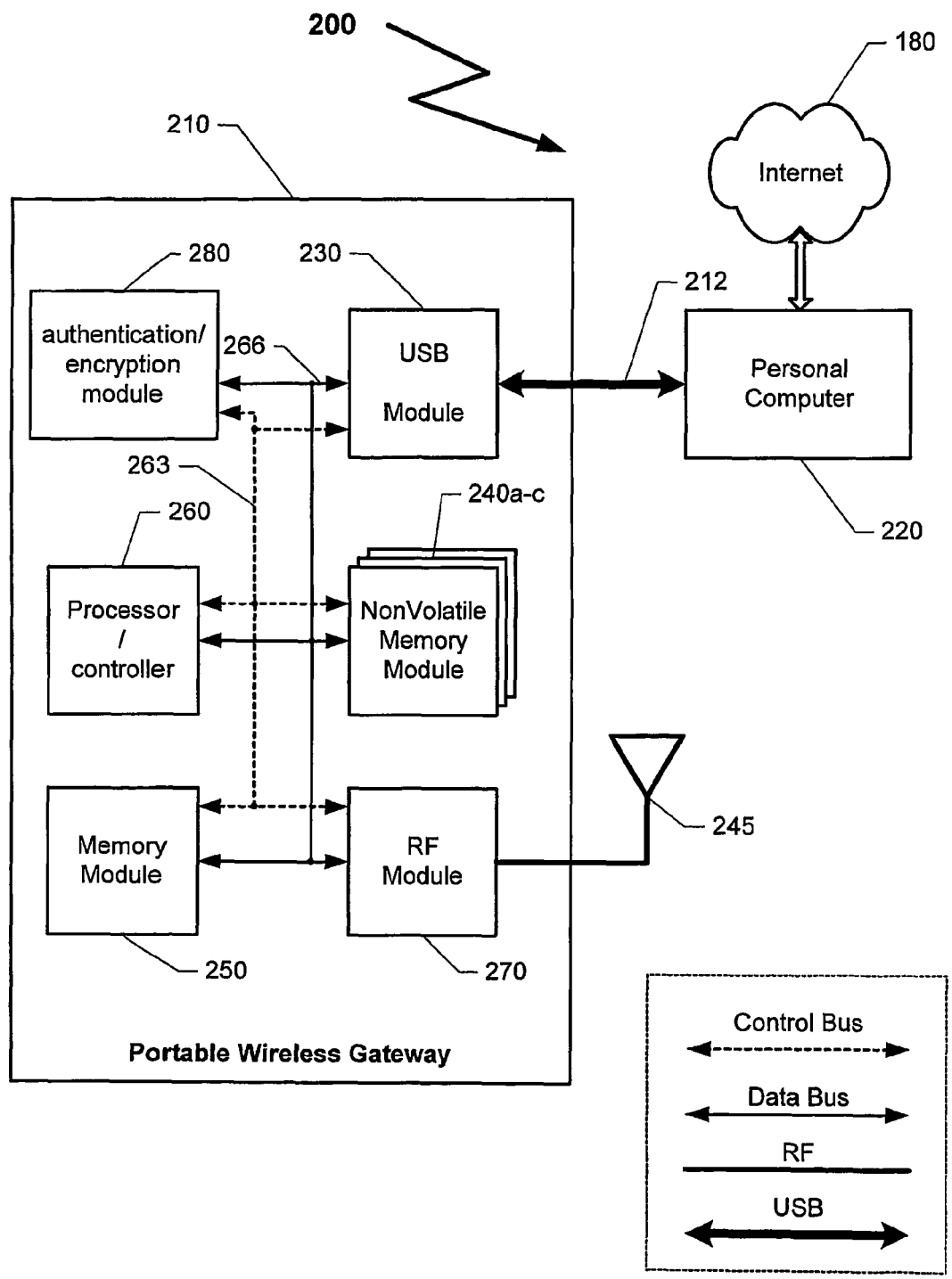
FIG. 2 is a schematic block diagram of the PWG part of the system according to an exemplary embodiment of the present invention.

FIG. 2 illustrates a schematic block diagram of the PWG part of the system 200 according to an exemplary embodiment of the present invention. The PWG section 200 of the system may comprise a PWG 210 and a PC 220 connected to the computer network 180. PC 220 may have Audio/Visual capabilities. PWG 210 together with PC 220 act as the interface between the user and/or the wearable device 101 (FIG. 1) and the central server 187 and/or the call center 185. PC 220 may act as a host platform having a USB host controller for controlling and managing all USB transfers on the USB bus.

PWG 210 may be implemented as a single unit that is plugged into the USB port of PC 220. PWG 210 may have the shape of a USB flash memory disk that is illustrated in U.S. design Pat. No. D 462,689 or D 468,090 the contents of which are incorporated herein by reference. However the present invention is not limited to this shape, other embodiments of the present invention may have other shapes or may be connected to other ports of PC 220.

PWG 210 may comprise a USB module 230, a non-volatile memory module such as flash memory, EEPROM, FRAM that may be logically divided into several non-volatile memory modules that are represented by three modules 240*a* to 240*c*, RF module 270, antenna 245, a memory 250, authentication/encryption module 280, and a processor/controller 260 that controls the operation of the different modules of PWG 210. PWG 210 may comprise two buses, a data bus 266 and a control bus 263 or any other serial or parallel bus structure. In other embodiments of the present invention the two logical buses data bus 266 and a control bus 263 may share the same physical bus.

PWG 210 collects medical data from at least one monitor equipment such as wearable device 101 (FIG. 1) via wireless communication. The data is sent to computer 220 over USB connection 212 and from PC 220 over the computer network 180 to the call center and/or the central server 187.

USB module 230 acts as the interface module between the controller 260 of PWG 210 and PC 220. USB module 230 may include the physical interface for receiving and transmitting electrical signals to and from PC 220 according to the communication protocol and a logical interface for decoding the address, synchronizing the signals and communicating with the controller 260. The incoming packets from PC 220 are parsed and transferred to controller 260 over the internal buses 266 and/or 263. In the other direction information from the controller 260 are received by USB module 230, packetized according to the USB protocol and sent over the USB 212 port to the PC 220. In case of using other type of communication port than USB, such as RS232, then USB module 230 may be replaced by an appropriate module.

Nonvolatile memory Module (NVMM) 240*a*-204*c* may be divided into several logical non-volatile memory modules. NVMM 240*a* may store the software that controls the operation of controller 260. NVMM 240*b* may store the operating software that is used by PC 220 for controlling the operation of the user site. This software may be loaded into PC 220 immediately after connecting the PWG 210 to the USB port 212. NVMM 240*c* may be used for storing the personal information of the user. The personal information may include authentication data of the user as well as medical information, such as the file history of the user, current results of medical measurements, the schedule for taking medicine, sensitivity information about medicines, or any type of data that may help a medical personal that take care of the user. The present invention is not limited to 3 modules of NVMM 240*a* to 240*c* and any other number of modules may be used. The operation of NVMM 240 is controlled by processor 260. Exemplary NVMM may be built of nonvolatile memory, such as but not limited to flash memory, EEPROM, FRAM, a section of NVMM 240 may be built of non-erasable memory modules such as EPROM, PROM, etc.

RF module 270 is used as the complementary communication unit to the communication unit 104 (FIG. 1) of the wearable device. RF module 270 may comprise an interface unit (not shown) that converts the data coming from the internal bus 266 and/or 263 according to the RF communication protocol and vice versa. The interface unit is connected in one side to bus 266 and/or 263 and on the other end to RF transmitter/receiver (not shown). The RF transmitter/receiver is connected to an antenna 245 that may be an external antenna or an internal antenna. RF module 270 and communication unit 104 may use a standard RF protocol, such as Bluetooth or IEEE 802.11 (wireless LAN) or any other technology or proprietary protocol. The RF frequency may be 433 MHz, 868 MHz, 915 MHz or any other frequency that may be used for such an application.

Other exemplary embodiments of the present invention may use wireless communication techniques other than RF, for example IR communication. In such an embodiment, the RF module will be replaced by an appropriate module having the appropriate transmitter/receiver and may have a lens/sensor instead of antenna 245.

Memory module 250 may be a combination of any type of short-term memory such as RAM, SRAM and DRAM etc. with long-term memory such as EPROM that is used to support the operation of the controller 260. The memory 250 may be used for storing the bootstrap program of controller 260, the current program, setting parameters for monitoring equipment 101 and may be used for intermediate buffer for data coming from/to the Medical Center 185 to/from the Monitoring equipments 101.

Controller 260 may be a computational device such as, but not limited to, a general-purpose microprocessor, a DSP, a micro-controller or a special ASIC designed for that purpose. In some embodiments of the present invention Controller 260 is used to control the operation of the internal modules of PWG 210, while PC 220 is used to control the operation of system 200 as well as the wearable device 101 (FIG. 1). In those embodiments, PC 220 may analyze the medical information that is coming from the wearable device 101 via PWG 210.

In other embodiments of the present invention the PC 220 is just used as an interface between PWG 210 and the Internet 180. In those embodiments the controller 260 may process the physiological measurements into medical information before transferring the results to the call center 185 via PC 220 and the Internet. In other embodiments of the present invention, processing the information may be done in the central server 187 (FIG. 1).

An exemplary embodiment of the present invention may comprise an authentication/encryption module 280. Authentication/encryption module 280 may be used in order to protect the privacy of the information that is stored in PWG 210.

PC 220 and/or the PWG 210 may be used as an intermediate buffer that stores commands and/or data, which requested by the user using the software running on the PC 220 or commands and/or data coming from the Medical Service center 185 (FIG. 1) to the monitoring equipment 101, until receiving a request from the monitoring equipment 101 to set communication with the PWG 210. The information coming from the Medical Center 185 and/or from the user may include data like, but not limited to, type of measurements that are needed, setting the sleeping period, setting the internal clock of the monitoring equipment etc. Upon setting the communication between the two, the monitoring equipment 101 asks the PWG 210 to retrieve the information that has been received from the medical center 185 and/or from the user during the recent sleeping period. In this method of operation, the PWG 210 and/or PC 220 is used as an intermediate buffer for calls coming from both sides either from the monitoring equipment 101 or from the medical center 185. The PWG 210 and/or PC 220 eliminate the need for the medical center as well as the monitoring equipment 101 to be on-line on the same time.

Figure 3:
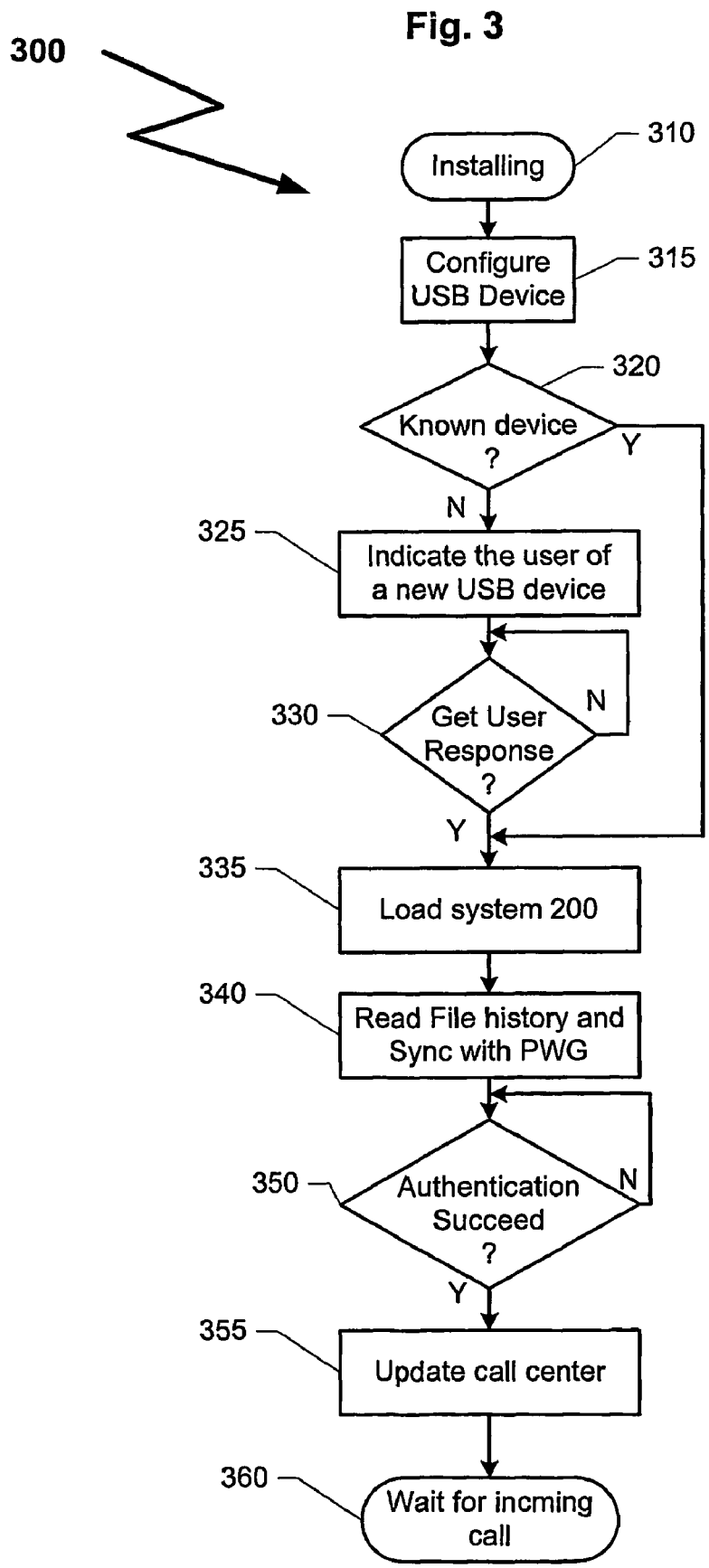
FIG. 3 is an exemplary flow diagram illustrating the installation of the PWG of FIG. 2.

FIG. 3 is an exemplary flow diagram illustrating the operation of PC 220 and PWG 210 during the set up, after installing the PWG 210 in a USB port 212 (FIG. 2). Upon installing 310 PWG 210 in the USB socket, a standard USB configuration process 315 takes place. In this process PC 220 configures the USB new device 210 and the mode of communication with USB device 210. Although there are many different methods for configuring USB devices, for the purposes of clarity only and without intending to be limiting, the present invention is explained in greater detail below with regard to a method in which PC 220 issues commands and requests to a USB device through one endpoint. PC 220 queries USB device 210 through the other endpoint for status changes, and receives related packets if any such packets are waiting to be received.

Then in step 320 PC 220 may check whether the driver for the new device exist in its library. If yes, PC 220 moves to step 335 and starts loading the software that performs the operation of PC 220. If not, PC 210 indicates to the user 325 about the new device and waits 330 for the loading of the driver of the PWG 210 by the user. The loading may be done from a portable media such as CD ROM or from the NVMM 240*b* of device 210 or through the Internet. In case of using the PWG 210 as the storage media of the driver, the PWG 210 upon installing and turn on, emulates a USB flash memory disk device, which is known to PC 220. Then the user may load 330 the driver from PWG 210 and continue to step 335.

After loading 335, PC 220 reads 340 the file history and the personal information of the user from NVMM 240*c* updates PWG 210 accordingly and synchronizes with PWG 210. Then PC 220 prompts the user to identify him and perform an authentication protocol. If 350 the authentication is successful, the PC 210 continues to step 355 and calls the call center 185, updates it with the current situation of the user and the current communication link to the system 200 via PC 220. If the authentication fails 350, PC 220 returns to step 340. This procedure may repeat for several times until the PC 220 sends a fail indication to the user.

Then PC 220 and PWG 210 may wait 360 for new call. The new call may come from the wearable device 101 (FIG. 1) or from the call center 185. The response of PGW 210 with PC 220 to incoming calls may be like the response of the remote gateway that is disclosed in the incorporated PCT applications (PCT/IL01/01187; PCT/IL02/00285; PCT/IL02/00995; PCT/IL02/00994) the contents of which are incorporated herein by reference.

FIG. 4 is an exemplary flow diagram illustrating the removal of the PWG 210 from the USB port 212. When the user desires to remove the PWG 210 from the PC 220, the user instructs PC 220 to disconnect 410 the PWG 210. Then PC 220 updates 415 the call center 185 (FIG. 1) and the central server 187 (FIG. 1) about the disconnection and exchange the required information before the disconnection. Then 420 PWG 210 is updated regarding the incoming disconnection. PC 220 updates NVMM 240*c* (FIG. 2) with the current information. If during this period of time there is a valid connection with the wearable device 101, the PWG 210 may update the wearable device too. Otherwise, the wearable device will be updated upon the next installation of PWG 210.

After the updating, PC 220 may indicate 430 to the user that the PWG 210 may be safety removed. And the task of PC 220 is terminated 440.

In the description and claims of the present application, each of the verbs, "comprise" "include" and "have", and conjugates thereof, are used to indicate that the object or objects of the verb are not necessarily a complete listing of members, components, elements or parts of the subject or subjects of the verb.

In this application the words "unit" and "module" are used interchangeably. Anything designated as a unit or module may be a stand-alone unit or a specialized module. A unit or a module may be modular or have modular aspects allowing it to be easily removed and replaced with another similar unit or module. Each unit or module may be any one of, or any combination of, software, hardware, and/or firmware.

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art. The scope of the invention is limited only by the following claims.

What is claimed is:

1. A system for remote measurements, the system comprising:
   (a) a measuring device for measuring at least one medical parameter of a user, wherein the measuring device comprises a communication module for wirelessly transmitting measured parameters and receiving data and instructions;
   (b) a portable wireless gateway, wherein the portable wireless gateway comprises a wireless module for wirelessly communicating with the measuring device and a computer interface module for communicating with a computer;

(c) a computer (PC) with a standard port to which the portable wireless gateway is connected to;
wherein the portable wireless gateway stores the following:
software used by the PC for operating the system;
personal information of the user; and
setting parameters for the measuring device;
wherein the portable wireless gateway is configured to load at least one of the software, the personal information, and setting parameters to the computer; and
wherein the computer is configured to download the software from the portable wireless gateway, and, using the software, to receive the measured parameters via the portable wireless gateway, to analyzes measured data and to alert the user.

2. The system of claim 1, further comprising:
(d) a central server being operative to communicate with the PC and to store and analyze measured data; and
(e) a computer network between the computer (PC) and the central server for carrying the communication between the two.

3. The system of claim 2 wherein the computer network is the Internet.

4. The system of claim 1, wherein the portable wireless gateway is connected to a Universal Serial Bus (USB) connector.

5. The system of claim 1, wherein the personal information stored in portable wireless gateway is used for at least one function selected from a group consisting of: authentication and encryption.

6. The system of claim 1, wherein the personal information contains medical data of the user.

7. The system of claim 1, wherein the portable wireless gateway emulates a USB flash memory disk device.

8. The system of claim 7, wherein the computer (PC) operates the software from the emulated USB flash memory disk device.

9. The system of claim 1, wherein the measuring device is wearable by a user.

10. The system of claim 1, wherein the measuring device is further comprising a movement sensor.

11. The system of claim 10, wherein the movement sensor is adapted for measuring the user's breathing.

12. The system of claim 1, wherein the measuring device is further comprising a smoke detector.

13. The system of claim 1, wherein the measuring device is further comprising a burglary alarm.

14. The system of claim 1, wherein the computer standard port is a USB port.

15. A portable wireless gateway suitable for use within a remote medical monitoring system that comprises a measuring unit, and a computer, the portable wireless gateway comprising:
a wireless communication unit operative to communicate with the measuring unit;
a non-volatile memory module containing: software used by the PC for operating the system, personal information of the user, and setting parameters for the measuring device;
a computer interface module operative to connect to the computer; and
a processing unit,
wherein after connecting the portable wireless gateway to the computer, the portable wireless gateway uploads at least one of the software and the personal information to the computer; and
the portable wireless gateway communicatively coupled via the wireless communication unit with the measuring unit, and in response to instructions, the processing unit being operable to receiving physiological data from the measuring unit through the wireless communication unit; processing the received physiological data and transferring the processed physiological data to the computer via the computer interface module;
whereby connecting the portable wireless gateway to a computer the computer becomes a part of the remote medical monitoring system during the period of the connection; and
wherein the software loaded and executed by the computer activates the measuring unit, receives medical information from the measuring unit via the portable wireless gateway, analyzes measured data, and alerts the user.

16. The portable wireless gateway of claim 15, wherein the connection between the portable wireless gateway and the computer is USB connection.

17. The portable wireless gateway of claim 15, wherein the non-volatile memory module stores personal information of the user, and wherein the processing unit is operative to process the physiological measurements into medical information.

18. The portable wireless gateway of claim 15, wherein the non-volatile memory module stores the software that will be operated by the computer for operating the remote medical monitoring system while connected to the portable wireless gateway.

* * * * *